United States Patent [19]
Wijayarathna

[11] Patent Number: 4,464,176
[45] Date of Patent: Aug. 7, 1984

[54] BLOOD VESSEL CATHETER FOR MEDICINE DELIVERY AND METHOD OF MANUFACTURE

[75] Inventor: Bandula Wijayarathna, Friendswood, Tex.

[73] Assignee: Mallinckrodt, Inc., St. Louis, Mo.

[21] Appl. No.: 385,334

[22] Filed: Jun. 4, 1982

[51] Int. Cl.³ .............................................. A61M 5/00
[52] U.S. Cl. ................................. 604/164; 604/264; 604/280
[58] Field of Search ..................... 604/52, 53, 93, 158, 604/164, 170, 239, 264, 280, 281, 283

[56] References Cited

U.S. PATENT DOCUMENTS

| | | | |
|---|---|---|---|
| 2,437,542 | 3/1948 | Krippendorf | 604/282 X |
| 3,605,750 | 9/1971 | Sheridan | 604/280 X |
| 4,044,765 | 8/1977 | Kline | 604/164 |
| 4,239,042 | 4/1979 | Asai | 604/266 X |
| 4,318,402 | 3/1982 | Vaillancourt | 604/280 |

OTHER PUBLICATIONS
Ganz-Edwards, "Coronary Infusion Catheter", Aug. 12, 1981.

Primary Examiner—Stephen C. Pellegrino
Attorney, Agent, or Firm—Bernard, Rothwell & Brown

[57] ABSTRACT

A catheter which is capable of delivering medicine into a blood vessel at a selected point, such as into a coronary artery, includes an outer tube which is joined to the outside diameter of an inner tube by drawing the tubes through a heated die. A distal portion of the outer tube extends beyond the distal end of the inner tube, and the outer tube is formed from a polymeric material having a substantially lower flexural modulus than the polymeric material of the inner tube so that the distal portion is relatively flexible for enabling insertion in a tortuous blood vessel. The inner diameters of the inner tube and the distal portion of the outer tube permit insertion of a guide wire therethrough for aiding in the insertion of the catheter.

17 Claims, 7 Drawing Figures

BLOOD VESSEL CATHETER FOR MEDICINE DELIVERY AND METHOD OF MANUFACTURE

TECHNICAL FIELD

The present invention relates to catheters for delivering medicine into blood vessels at selected points, for example, a coronary infusion catheter designed to be inserted through an installed angiography catheter to extend beyond the angiography catheter so that a medicine such as a thrombolytic drug or other drug can be delivered to a selected point in a coronary artery.

BACKGROUND ART

The prior art contains a number of blood vessel catheters including coronary infusion catheters which are inserted through coronary angiography catheters to position the distal ends of the infusion catheters at selected points in coronary arteries. Coronary infusion catheters include the following types: (1) a polytetrafluoroethylene tube of uniform construction; (2) a PVC tube shrunk onto a metal coil spring body with a distal 20 cm section of the tube extending past the end of the spring body and having a shrunken diameter to form a more flexible distal section to aid in negotiating curves; and (3) a polymer tube having a body section with a reinforcing braid included in the tube wall wherein a distal 20 cm section of the tube extending from the body section does not contain the reinforcing braid. These infusion catheters are usually inserted through a previously installed angiography catheter with the distal end being advanced, under fluoroscopic guidance, from the end of the angiography catheter to the desired site. Difficulty has sometimes been experienced in positioning of prior art catheters in some blood vessels, for example in the left circumflex coronary artery. Vascular trauma has also been experienced by various types of prior art catheters.

Uniform tube type coronary infusion cathethers, such as the polytetrafluoroethylene tube of 2.5 French size, are generally too stiff for the distal end to negotiate tortuous blood vessels without traumatizing the vessels and are generally too flexible to possess desired torque and column characteristics. The torque characteristic concerns the ability to transmit rotational movement from one end of the catheter to the other; catheters must sometimes be rotated in order to direct a curved distal end of the catheter into a selected branch vessel or to follow a vessel curve. The column characteristic concerns the ability to resist buckling of the catheter while being pushed; buckling at the entrance of a guiding catheter or within a vessel produces kinks or sharp bends which make insertion more difficult, or prevents insertion of the distal end of the catheter to the desired site in the blood vessel. Guide wires, i.e. tightly coiled fine metal springs, with or without precurved ends are commonly inserted inside catheters to render the catheters less flexible and to direct the distal end of the catheter in the desired direction. Such guide wires generally can not substantially improve torque characteristics of the catheter, and because of uniformity in flexibility or stiffness throughout their length, can not provide the degree of variation in flexibility or stiffness required to negotiate turns and simultaneously resist buckling.

The prior art catheter type with the PVC tube shrunk on the metal coil spring does provide a variation in stiffness or flexibility between the body section secured on the spring and the distal portion extending from the body portion. However, such coronary infusion catheters of a favorable size, i.e. 2.5 French in the body sections and 2.0 French in the distal section, have relatively small internal diameters through the coil springs and the distal sections preventing insertion of a guide wire and also restricting the flow of medicine. Additionally, the tube wall is relatively thick in the distal section because of shrinkage of a larger tube size limiting the degree of flexibility, and this type of catheter includes a rigid radiopaque tip which tends to traumatize blood vessels.

The reinforced braid type coronary infusion catheter is generally too large, i.e. 4 French in size, and too stiff in its distal section to be readily inserted without excessive risk of vessel traumatization.

SUMMARY OF THE INVENTION

In accordance with a first aspect of the present invention, a catheter includes inner and outer laminated coaxial tubes of polymeric material wherein the inner tube is formed of a polymeric material having a relatively high strength and a relatively high flexural modulus, the outer tube is relatively softer and more flexible and has a distal portion extending beyond the distal end of the inner tube, and has a slightly enlarged section of the outer tube bridging the distal end of the inner tube to reinforce the outer tube.

In accordance a second aspect of the invention, inner and outer tubes assembled on a mandrel are drawn through a heated die to laminate the outer tube to the inner tube and to form a catheter. A distal section of the outer tube extends beyond the distal end of the inner tube to form a soft, flexible end portion on the catheter.

An object of the invention is to construct a catheter having improved flexural variations in order to enable insertion into vessels while resisting buckling.

Another object of the invention is to provide a blood vessel catheter with a lesser tendency for traumatizing blood vessels.

One advantage of the invention is that a hard-soft polymer combination in the body of the catheter provides a thin walled catheter with excellent torque and column characteristics to enable the catheter to be easily inserted into a blood vessel.

Another advantage of the invention is that a guide wire may be inserted into the catheter, including into a distal flexible portion of the catheter, to aid in insertion of the catheter.

Other objects, advantages and features of the invention will be apparent from the following description of the preferred embodiment taken in conjunction with the accompanying drawings.

DESCRIPTION OF THE PREFERRED EMBODIMENTS

Figure 1:
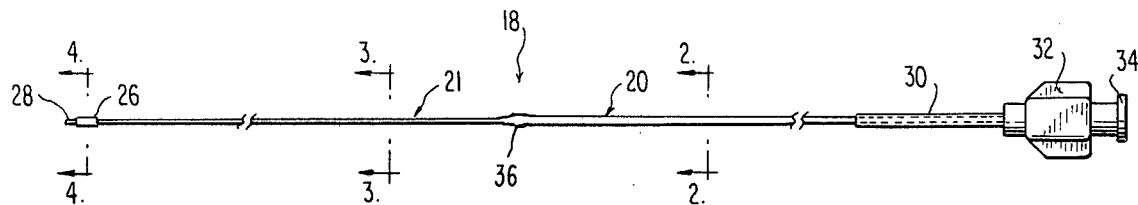
FIG. 1 is a plan view of a coronary infusion catheter, with portions broken away, constructed in accordance with the invention.
Figure 2:
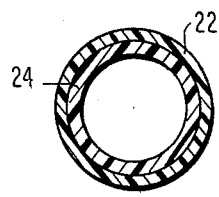
FIG. 2 is a cross-section taken at line 2—2 in FIG. 1.
Figure 3:
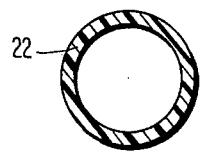
FIG. 3 is a cross-section taken at line 3—3 in FIG. 1.

As illustrated in FIGS. 1-4, a coronary infusion cathether indicated generally at 18 and constructed in accordance with an embodiment of the invention includes a main section indicated generally at 20 formed by an outer polymeric tube 22 coaxially laminated on an inner polymeric tube 24, and a distal portion or section indicated generally at 21 wherein the inner tube is absent. The inner tube 24 is a polymer having relatively high strength and a relatively high flexural modulus, while the outer tube 22 is a softer polymer having a relatively lower flexural modulus. Thus, the distal portion 21 is relatively flexible, permitting the distal portion to negotiate curves in tortuous arteries into which the catheter is being inserted. The strength and stiffness of the inner tube 24 imparts the desired torque and column characteristics to the main section 20. The combination of hard-soft polymer tubes permits the catheter to have a relatively large inside diameter, enabling the insertion of a guide wire, such as a coiled spring-like guide wire, through both sections 20 and 21 to aid in positioning the distal end of the catheter in the desired point in an artery.

Preferably, the polymer of the inner tube 24 has a flexural modulus within the range from about 50,000 to 300,000 psi (3,515 to 21,100 kg/cm$^2$) and the polymer of the outer tube 22 has a flexural modulus in the range from about 10,000 to 50,000 psi (703 to 3,515 kg/cm$^2$). Examples of higher strength and higher modulus polymeric materials suitable for the inner tube 24 include nylons, high density polyethylenes, and aramid resins. Examples of soft plastic materials with lower modulus suitable for the outer tube 22 include urethanes, PVC, and low density polyethylenes.

Figure 4:
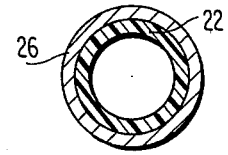
FIG. 4 is a cross-section taken at line 4—4 in FIG. 1.

In the distal section 21, the outside diameter of the outer tube 22 is reduced without any increase in wall thickness, rendering the section 21 even more flexible. A radiopaque member 26 is secured to the distal portion 21 adjacent to the distal end of the catheter. The radiopaque member 26 of FIGS. 1 and 4 is a short metal sleeve, 1 to 2 mm in length, secured on the outside of the tube 22. Examples of suitable metals for the sleeve 26 include 10 k gold, tantalum, tungsten, or any other radiopaque metal suitable for insertion in a blood vessel. The sleeve 26 is spaced slightly, 1 to 5 mm, from the distal end of the tube 22, leaving an end portion 28 of the tube 22 extending from the member 26. The distal end portion 28 is designed to avoid trauma to blood vessels caused by hard tips.

At the opposite end of the catheter, a short section of reinforcing tube is firmly secured over the end portion of the combined tubes 22 and 24. A luer 32 with a hub 34 suitable for connecting the catheter to other devices is fastened on the ends of the tubes 30, 22, and 24.

An example of the coronary infusion catheter has an overall length of about 135 centimeters with the distal section 21 being about 20 centimeters in length. The main section 20 has a outside diameter of about 0.039±0.002 inches (0.99±0.05 mm) and an inside diameter of about 0.025±0.002 inches (0.64±0.05 mm). The distal section 21 has an outside diameter of about 0.030±0.001 inches (0.76±0.03 mm) and an inside diameter of about 0.022±0.001 inches (0.56±0.03 mm). The radiopaque metal sleeve 26 is approximately 2 mm in length and has an outside diameter of about 0.034±0.0005 inches (0.86±0.02 mm) and an inside diameter of about 0.029±0.0005 inches (0.74±0.02 mm). The protruding soft end 28 is about 2 mm in length.

The coronary infusion catheter is manufactured by extruding the inner and outer tubes 22 and 24 so that the inner tube 22 can be slipped into the outer tube 24 snugly. Examples of suitable size extruded tubes include an inner tube having an outside diameter of about 0.040 inches (1.02 mm) and an inside diameter of about 0.027 inches (0.7 mm), and an outer tube having an outside diameter of about 0.055 (1.4 mm) and an inside diameter of about 0.043 inches (1.09 mm). The inner tube 22 is inserted into the outer tube such that a distal portion of the outer tube extends past the distal end of the inner tube. A wire mandrel of the desired inner diameter size, e.g. 0.025 inches (0.64 mm), is introduced through the inner tube in its entire length. Then, the assembly of the mandrel, the inner tube and the outer tube, is drawn by pushing or pulling through a proper size hole in a hot brass, stainless steel, or other metal die. The metal die is heated sufficiently to aid in plasticizing the polymer of the tubes, laminating the tubes together, and molding the inner tube to the size of the wire mandrel. During the drawing process, the pulling can be toward the distal portion 21 stopping just short of the distal end of the inner tube, thus causing the distal portion 21 to be extended in length due to extrusion or remolding of a portion of the polymer in the outer tube in the die. In the next procedure, a wire mandrel of appropriate diameter, e.g. 0.022 inches (0.56 mm), is inserted in the distal section 21 of the outer tube 22 and the distal section 21 is pulled through a second metal die having a hole size smaller than the first metal dye for producing the reduced diameter of the distal portion 21. The drawing can be from the distal end of the distal section 21 toward the distal end of the inner tube stopping just short of the distal end of the inner tube. Thus there is left a slightly enlarged non-drawn portion 36, e.g. about 4 mm in length, of the outer tube 22 bridging the distal end of the inner tube 24 to produce additional strength to prevent breakage of the outer tube at the distal end of the inner tube. The ends of the catheter are then trimmed, and the metal sleeve 26 is attached by stretching the end portion of the tube section 21 to reduce its diameter, and positioning the sleeve 26 over the end portion, forcing the sleeve on to a non stretched portion where the elasticity of the tube secures the metal sleeve on to the tube, the stretched end being cut off. Optionally, an adhesive may be used to secure or aid in securing the sleeve 26. Then, the reinforcing tube 30 is slipped on the opposite end of the catheter and the luer 32 is bonded to the ends of the tubes 22, 24 and 30.

Figure 7:
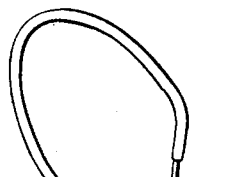
FIG. 7 is a cross-section view of the catheter of FIG. 1 inserted in a conventional angiography catheter to illustrate employment of the catheter of the invention.

In use of the coronary infusion catheter 18, a conventional angiography catheter 40, shown in FIG. 7, is inserted in the artery in a conventional manner. A conventional side arm "Y" adapter is attached to the hub of the angiography catheter. The air may be removed from the coronary infusion catheter 7 by distilled water or saline solution from a syringe or other apparatus attached to the hub 34. The catheter 18 is then inserted through the straight arm of the "Y" adapter with the sealing ring in the straight arm being tightened slightly to minimize bleeding, yet allow the advancement of the catheter approximately 80–90 centimeters into the angiography catheter. A guide wire 44, such as a fine coiled stainless steel wire of 0.018 inch (0.46 mm) diameter, with or without a curved end may have been previously inserted in the catheter 18.

Further advancement of the coronary infusion catheter is performed under fluoroscopic guidance. The radiopaque member 26 and the catheter itself are readily visible, and contrast material may be injected into the artery through the side arm of the "Y" adapter to enable viewing of the positioning of the distal end of the catheter 18 in the artery. The guide wire 44, inserted into the catheter 18 may extend completely through the catheter 18 including the distal portion 24. The guide wire adds a degree of stiffness, particularly to a selected length of the distal portion, during the insertion of the catheter 18 past the catheter 40. Adjustment of the position of the guide wire 44 and rotation of the catheter and guide wire can be utilized in advancing and directing the tip 28 and distal portion 24 to a selected point in the arteries. After the infusion catheter is in the selected position, the guide wire 44 may be removed and the hub 34 attached to a suitable supply apparatus for injecting medicine into the artery.

The catheter 18, having a substantially large inside opening relative to its outside diameter, enables a substantial rate of medicine to be fed, as well as enabling the insertion of the guide wire 44. Previous catheters could not utilize a relatively flexible and floppy distal portion for negotiating torturous curvatures combined with selective insertion of a guide wire to aid in guiding the catheter. Further, the present catheter has greatly improved torque and column characteristics compared to previous catheters, and the soft tip 28 is less traumatic to blood vessels.

Figure 5:
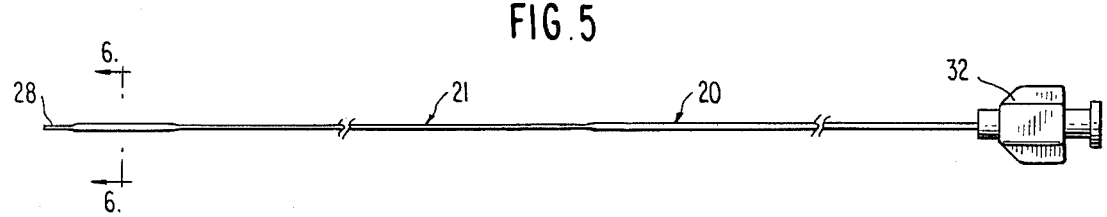
FIG. 5 is a plan view of a modified coronary infusion catheter, with portions broken away, constructed in accordance with the invention.
Figure 6:
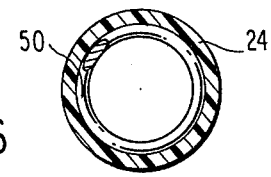
FIG. 6 is a cross-section view taken at line 6—6 in FIG. 5.

A modified coronary infusion catheter is shown in FIGS. 5 and 6, wherein a radiopaque coil spring 50 is secured inside of the end portion of the distal section 21 of the catheter in place of the exterior band 26 of FIG. 1. The coil spring 50 is inserted by swelling the end portion of the tube 24 by means of a solvent, inserting the section of spring 50, and allowing the end portion of the tube 24 to dry, shrinking the end portion to secure the spring member 50. The spring member 50 may have a substantial length, for example 0.5 to 2 centimeters, and has sufficient flexibility to permit bending within sharply curved passageways. The radiopaque spring 50 is installed leaving a flexible end portion 28 of the tube 24 extending beyond the member 50, for example 2 to 5 millimeters.

Alternatively, the short metal band 26 of FIG. 1 may be secured inside of the end portion of the tube 24 similar to the spring 50, or the spring 50 may be secured on the outside of the end portion of the tube section 21, similar to the band 26.

Since many modifications, variations, and changes in detail may be made to the above described embodiment, it is intended that all matter described in the foregoing description and shown on the accompanying drawings be interpreted as illustrative and not in a limiting sense.

What is claimed is:

1. A catheter which is capable of delivering drugs into a blood vessel at a selected point, comprising:
    an inner tube;
    an outer tube surrounding and being laminated to the outside of the inner tube;
    said outer tube having a distal portion extending beyond a distal end of the inner tube;
    said inner tube being formed from a high strength polymeric material having a first flexural modulus;
    said outer tube being formed from a soft plastic material having a second flexural modulus which is substantially less than the first modulus; and
    said inner tube and said distal section of the outer tube having inner diameters permitting insertion of a guide wire therein;
    wherein the distal section of the outer tube has an outer diameter which is less than the outer diameter of the remaining portion of the outer tube, and the outer tube has a slightly enlarged section bridging the distal end of the inner tube.

2. A catheter as claimed in claim 1 wherein the first flexural modulus is in the range from about 50,000 to 300,000 psi, and the second flexural modulus is in the range from about 10,000 to 50,000 psi.

3. A catheter as claimed in claim 1 including a rigid radiopaque member secured to the distal section of the outer tube adjacent the distal end thereof leaving an end portion of the distal section free of the radiopaque member.

4. A catheter as claimed in claim 3 wherein the radiopaque member is a radiopaque metal sleeve.

5. A catheter as claimed in claim 3 wherein the radiopaque member is a radiopaque metal coil.

6. A catheter as claimed in claim 4 or 5 wherein the radiopaque member is secured on the outside of the distal section of the outer tube.

7. A catheter as claimed in claim 4 or 5 wherein the radiopaque member is secured on the inside of the distal section of the outer tube.

8. A catheter as claimed in claim 1, 2, 4 or 5, including a luer having a hub fastened to the end opposite to the distal end for connecting the catheter to other devices, and a guide wire for insertion in the catheter to aid in placement thereof.

9. A catheter as claimed in claim 8 wherein the laminated inner and outer tubes have an outside diameter of about 0.039 inches and an inside diameter of about 0.025 inches, and the distal section has an outside diameter of about 0.030 inches and an inside diameter of about 0.022 inches.

10. A catheter as claimed in claim 8, wherein the outer tube includes a slightly enlarged portion bridging the distal end of the inner tube.

11. A method of manufacturing a catheter which is capable of delivering drugs into a blood vessel at a selected point, comprising the steps of:
    inserting an inner tube of high-strength, higher-flexural modulus polymeric material into an outer tube of soft, lower flexural modulus polymeric material leaving a distal section of the outer tube extending from a distal end of the inner tube;
    inserting a wire mandrel through the inner tube;
    drawing the assembled tubes and mandrel through a heated die to laminate the outer tube on the inner tube; and
    removing the mandrel.

12. A method as claimed in claim 11 including the further steps of inserting a wire mandrel in the distal section of the outer tube, and drawing the distal section of the outer tube through a second heated die to reduce the diameter of the distal section to a lesser dimension than the remaining portion of the outer tube.

13. A method as claimed in claim 11 or 12 including the step of securing a radiopaque metal member to the distal section of the outer tube adjacent to, but slightly spaced from the distal end of the outer tube.

14. A method as claimed in claim 12 wherein the securing step includes stretching an end portion of the distal section of the outer tube to reduce its diameter, inserting a sleeve-like radiopaque metal member over the reduced diameter end portion, forcing the metal sleeve onto a non-stretched portion of the outer tube, and cutting the stretched portion from the outer tube.

15. A method as claimed in claim 13 wherein the securing step includes swelling an end section of the distal portion of the outer tube by means of a solvent, inserting a sleeve-like radiopaque metal member into the swelled end portion of the outer tube, and drying the swelled end portion of the outer tube to shrink the end portion and secure the metal member.

16. A method as claimed in claim 11 or 12 wherein the step of drawing the assembled tubes and mandrel includes drawing a further portion of the outer tube past the distal end of the inner tube to increase the length of the distal section of the outer tube extending from the distal end of the inner tube.

17. A method as claimed in claim 12 where the drawing steps are stopped short of the distal end of the inner tube to leave an enlarged portion of the outer tube bridging the distal end of the inner tube.

* * * * *